United States Patent
Haley

(10) Patent No.: US 10,490,306 B2
(45) Date of Patent: Nov. 26, 2019

(54) MEDICAL INFORMATION TRANSLATION SYSTEM

(71) Applicant: CERNER INNOVATION, INC., Kansas City, KS (US)

(72) Inventor: John D. Haley, Chester Springs, PA (US)

(73) Assignee: CERNER INNOVATION, INC., Kansas City, KS (US)

(*) Notice: Subject to any disclaimer, the term of this patent is extended or adjusted under 35 U.S.C. 154(b) by 664 days.

(21) Appl. No.: 14/627,756

(22) Filed: Feb. 20, 2015

(65) Prior Publication Data

US 2016/0246946 A1 Aug. 25, 2016

(51) Int. Cl.
| | |
|---|---|
| *G16H 15/00* | (2018.01) |
| *G16H 10/60* | (2018.01) |
| *G06F 19/00* | (2018.01) |
| *G06F 16/951* | (2019.01) |
| *G06F 16/22* | (2019.01) |
| *G06F 16/2457* | (2019.01) |

(Continued)

(52) U.S. Cl.
CPC .......... *G16H 15/00* (2018.01); *G06F 16/2291* (2019.01); *G06F 16/24575* (2019.01); *G06F 16/951* (2019.01); *G06F 17/2785* (2013.01); *G06F 17/289* (2013.01); *G06F 19/3418* (2013.01); *G16H 10/60* (2018.01)

(58) Field of Classification Search
CPC ...... G06Q 50/22; G06Q 50/24; G06F 19/322; G06F 17/211
USPC ......................................................... 705/2–4
See application file for complete search history.

(56) References Cited

U.S. PATENT DOCUMENTS

| 5,251,316 A | 10/1993 | Anick et al. |
| 5,560,005 A | 9/1996 | Hoover et al. |

(Continued)

FOREIGN PATENT DOCUMENTS

| EP | 722140 | 7/1996 |
| EP | 1 304 645 | 4/2003 |

(Continued)

OTHER PUBLICATIONS

Luciano, Joanne, "The Translational Medicine Ontology and Knowledge Base: driving personalized medicine by bridging the gap between bench and bedside," Bio-Ontologies 2010: Semantic Applications in Life Sciences (Year: 2010).*

(Continued)

*Primary Examiner* — John P Go
(74) *Attorney, Agent, or Firm* — Shook, Hardy & Bacon L.L.P.

(57) ABSTRACT

Medical information is communicated between different entities. Personalized models of peoples' understanding of a medical field are created. Role information is used to create the personalized model. More information than mere role may be used for at least one of the personalized models, such as information on past medical history. The personalized models link to various subsets of base medical ontologies for one or more medical subjects. The concepts and relationships in these ontologies formed by the linking may be matched, providing a translation from one personalized model to another. The terminology with similar or the same concepts and/or relationships is output for a given user based on their model.

16 Claims, 2 Drawing Sheets

(51) Int. Cl.
*G06F 17/27* (2006.01)
*G06F 17/28* (2006.01)

(56) References Cited

U.S. PATENT DOCUMENTS

| | | |
|---|---|---|
| 5,642,518 A | 6/1997 | Kiyama et al. |
| 5,652,898 A | 7/1997 | Kaji |
| 5,664,109 A | 9/1997 | Johnson et al. |
| 5,712,989 A | 1/1998 | Johnson et al. |
| 5,715,453 A | 2/1998 | Stewart |
| 5,724,575 A | 3/1998 | Hoover et al. |
| 5,740,425 A | 4/1998 | Povilus |
| 5,784,635 A | 7/1998 | McCallum |
| 5,809,471 A | 9/1998 | Brodsky |
| 5,809,476 A | 9/1998 | Ryan |
| 5,819,263 A | 10/1998 | Bromley et al. |
| 5,832,450 A | 11/1998 | Myers et al. |
| 5,867,821 A | 2/1999 | Ballantyne et al. |
| 5,911,687 A | 6/1999 | Sato et al. |
| 5,913,210 A | 6/1999 | Call |
| 5,915,240 A | 6/1999 | Karpf |
| 5,924,074 A | 7/1999 | Evans |
| 5,960,404 A | 9/1999 | Chaar et al. |
| 5,970,463 A | 10/1999 | Cave et al. |
| 5,970,492 A | 10/1999 | Nielsen |
| 5,987,472 A | 11/1999 | Serafin |
| 5,991,728 A | 11/1999 | Debusk et al. |
| 6,014,629 A | 1/2000 | Debruin |
| 6,018,713 A | 1/2000 | Coli et al. |
| 6,055,494 A | 4/2000 | Friedman |
| 6,055,516 A | 4/2000 | Johnson et al. |
| 6,058,375 A | 5/2000 | Park |
| 6,067,548 A | 5/2000 | Cheng |
| 6,072,493 A | 6/2000 | Driskell et al. |
| 6,112,183 A | 8/2000 | Swanson et al. |
| 6,112,209 A | 8/2000 | Gusack |
| 6,154,738 A | 11/2000 | Call |
| 6,163,781 A | 12/2000 | Wess |
| 6,173,253 B1 | 1/2001 | Abe |
| 6,182,029 B1 | 1/2001 | Friedman |
| 6,223,164 B1 | 4/2001 | Seare et al. |
| 6,260,021 B1 | 7/2001 | Wong et al. |
| 6,263,330 B1 | 7/2001 | Bessette |
| 6,282,508 B1 | 8/2001 | Kimura et al. |
| 6,301,584 B1 | 10/2001 | Ranger |
| 6,311,163 B1 | 10/2001 | Sheehan et al. |
| 6,311,192 B1 | 10/2001 | Rosenthal et al. |
| 6,314,556 B1 | 11/2001 | Debusk et al. |
| 6,345,245 B1 | 2/2002 | Sugiyama et al. |
| 6,347,329 B1 | 2/2002 | Evans |
| 6,430,541 B1 | 8/2002 | Brown et al. |
| 6,430,554 B1 | 8/2002 | Rothschild |
| 6,442,524 B1 * | 8/2002 | Ecker .................. G06F 17/2755 704/257 |
| 6,484,144 B2 | 11/2002 | Martin et al. |
| 6,485,869 B2 | 11/2002 | Tsai et al. |
| 6,510,434 B1 | 1/2003 | Anderson et al. |
| 6,510,989 B1 | 1/2003 | Ortega |
| 6,535,874 B2 | 3/2003 | Purcell |
| 6,542,933 B1 | 4/2003 | Durst et al. |
| 6,578,030 B1 | 6/2003 | Wilmsen et al. |
| 6,581,035 B1 | 6/2003 | Madan et al. |
| 6,708,161 B2 | 3/2004 | Tenorio et al. |
| 6,775,660 B2 | 8/2004 | Lin et al. |
| 6,785,671 B1 | 8/2004 | Bailey et al. |
| 6,785,869 B1 | 8/2004 | Berstis |
| 6,789,057 B1 | 9/2004 | Morimoto et al. |
| 6,901,255 B2 | 5/2005 | Shostak |
| 6,915,265 B1 | 7/2005 | Johnson |
| 7,020,618 B1 * | 3/2006 | Ward ............... G06Q 10/06311 705/2 |
| 7,062,509 B1 | 6/2006 | Nenov et al. |
| 7,392,237 B2 | 6/2008 | Pratt |
| 7,464,021 B1 | 12/2008 | Myers |
| 7,580,831 B2 | 8/2009 | Haskell et al. |
| 7,788,111 B2 | 8/2010 | Haskell et al. |
| 8,856,156 B1 | 10/2014 | McNair |
| 2001/0001144 A1 | 5/2001 | Kapp |
| 2001/0027403 A1 | 10/2001 | Peterson et al. |
| 2001/0029492 A1 | 10/2001 | Uchikata |
| 2001/0037227 A1 | 11/2001 | McInnis et al. |
| 2001/0041992 A1 | 11/2001 | Lewis et al. |
| 2001/0051879 A1 | 12/2001 | Johnson |
| 2001/0051880 A1 | 12/2001 | Schurenberg et al. |
| 2001/0051889 A1 | 12/2001 | Haney |
| 2002/0007284 A1 | 1/2002 | Schurenberg et al. |
| 2002/0007287 A1 | 1/2002 | Straube et al. |
| 2002/0018066 A1 | 2/2002 | Vizer |
| 2002/0023067 A1 | 2/2002 | Garland et al. |
| 2002/0046346 A1 | 4/2002 | Evans |
| 2002/0055917 A1 | 5/2002 | Muraca |
| 2002/0059107 A1 | 5/2002 | Reich et al. |
| 2002/0059201 A1 | 5/2002 | Work |
| 2002/0059204 A1 | 5/2002 | Harris |
| 2002/0059251 A1 | 5/2002 | Stern |
| 2002/0082868 A1 | 6/2002 | Pories et al. |
| 2002/0099622 A1 | 7/2002 | Suttile et al. |
| 2002/0107861 A1 | 8/2002 | Clendinning et al. |
| 2002/0111870 A1 | 8/2002 | Chinnappan et al. |
| 2002/0128871 A1 | 9/2002 | Adamson et al. |
| 2002/0129031 A1 | 9/2002 | Lau et al. |
| 2002/0161745 A1 | 10/2002 | Wu |
| 2003/0005464 A1 | 1/2003 | Gropper et al. |
| 2003/0074225 A1 | 4/2003 | Borsand et al. |
| 2003/0078813 A1 | 4/2003 | Haskell et al. |
| 2003/0078911 A1 | 4/2003 | Haskell et al. |
| 2003/0115129 A1 | 6/2003 | Feaver et al. |
| 2003/0177111 A1 | 9/2003 | Egendorf et al. |
| 2003/0233251 A1 | 12/2003 | Haskell et al. |
| 2003/0233252 A1 | 12/2003 | Haskell et al. |
| 2004/0059728 A1 | 3/2004 | Miller et al. |
| 2004/0167892 A1 * | 8/2004 | Kirshenbaum ..... G06F 17/2795 |
| 2005/0027566 A1 | 2/2005 | Haskell |
| 2005/0170863 A1 | 8/2005 | Shostak |
| 2006/0049936 A1 | 3/2006 | Colins et al. |
| 2006/0053098 A1 * | 3/2006 | Gardner ................. G06F 16/367 |
| 2006/0167738 A1 | 7/2006 | Spear et al. |
| 2007/0004971 A1 | 1/2007 | Riley et al. |
| 2008/0215365 A1 * | 9/2008 | Croan .................. G06F 19/3418 705/2 |
| 2008/0270438 A1 * | 10/2008 | Aronson ................ G16H 10/40 |
| 2010/0036676 A1 * | 2/2010 | Safdi .................... G06F 19/321 705/2 |
| 2012/0059669 A1 * | 3/2012 | Whittenburg ........... G06F 19/00 705/3 |
| 2012/0173475 A1 | 7/2012 | Ash et al. |
| 2012/0215555 A1 * | 8/2012 | Sharma ................ G06Q 10/06 705/2 |
| 2014/0136236 A1 * | 5/2014 | Lee ......................... G16H 10/60 705/3 |

FOREIGN PATENT DOCUMENTS

| | | | |
|---|---|---|---|
| GB | 2320111 | 6/1998 | |
| WO | 96 41288 | 12/1996 | |
| WO | 97 32271 | 9/1997 | |
| WO | 9832289 | 7/1998 | |
| WO | 01 06357 | 1/2001 | |
| WO | WO-2005008358 A2 * | 1/2005 | ......... G06F 21/6218 |

OTHER PUBLICATIONS

"SQLData SOAP Server" Jan. 25, 2001 SQLData Systems Inc., http://web.archive.org/web/20010202090100/http://sqldata.com/soap.htm.

"SOAP for Java" Apr. 28, 2000 IBM. http://www.alphaworks.ibm.com/tech/soap4j/.

"Simple Object Access Protocol (SOAP) 1.1", May 8, 2000 W3C et al. http://www.w3.org/TR/2000/NOTE-SOAP-20000508/.

"e*Index Global Identifier—Know Your Customer", printed Jul. 31, 2001 http://www.seebeyond.com/projects/eindex.html.

(56) References Cited

OTHER PUBLICATIONS

"e*Index Global Identifier—In Depth", printed Jul. 31, 2001, http://www.seebeyond.com/products/eindexInDepth.html.
"eBusiness Integration—It's not just B2B", printed on Jul. 31, 2001, http://seebeyond.com/products.
Joseph Ingenerf, et al., "Standardized terminological services enabling semantic interoperability between distributed and heterogeneous systems", International Journal of Medical Informatics 64 (2001) 223-240, Elsevier Scientific Publishers.
P.L. Elkin et al., "Automated enhancement of description logic-defined terminologies to facilitate mapping to ICD9-CM", Journal of Biomedical Informatics Academic Press USA, vol. 35: Oct. 5-6, 2002 pp. 281-288.
S.K. Bechhofer, et al., "Terminologies and Terminology Servers for Information Environments", Software Technology and Engineering Practice, 1997, Proceedings, Eighth IEEE International Workshop on Incorporating Computer Aided Software Engineering London, UK Jul. 14-18, 1997, Los Alamitos, CA USA, IEEE Comput. Soc. US, Jul. 14, 1997, pp. 484-497.
A.L. Rector, et al., "A Terminology Server for Medical Language and Medical Information Systems", International Medical Informatics Association, WG 5 Working Conference, May 1994 pp. 1-16.
R. Nikolai, et al., "Thesaurus Federations: A Framework for the Flexible Integration of Heterogenous, Autonomous Thesauri", Research and Technology Advances in Digital Libraries, 1998, ADL 98, Proceedings IEEE International Forum on Santa Barbara, CA USA Apr. 22-24, 1998. Los Alamitos, CA, USA IEEE Comput Soc. US, Apr. 22, 1998 pp. 46-55.
Hong Yu, et al., "Representing Genomic Knowledge in the UMLS Semantic Network" AMIA Annual Symposium a Donference fo the American Medical Informatics Association. Proceedings, Proceedings of AMIA Annual Symposium the Emergence of Internetable Health Care Systems That Really Work, Nov. 6, 1999 pp. 181-185.
Henery J. Lowe, et al., "The Image Engine HPCC Project. A Medical digital library system suing agent-based technology to create an Integrated view of the electronic medical record", Digital Libraries, 1996. ADL 1996, Proceedings of the Third Forum on Research and Technology Advances in Washington, DC, USA May 13-15, 1996. Los Alamitos, CA USA, IEEE Comput. Soc. US May 13, 1996 pp. 45-56.
International Search Report of International Application Serial No. PCT/US2004/021795 dated Jun. 22, 2005.
Signature Product Description information Jun. 1985.
"Structuring the Observatory Data", System Guide for Administrators, pp. 53-54.
"Health Supplier", printed on Jun. 7, 2002 http://www.healthtrade.com/tw/en/left/healthsupplier-en.htm.
"Organized Profile (OP Form): Example 1—VARANT Ltd", printed on Jun. 7, 2002 http://www.unece.org/ceiproj/ex1op.htm.
Healthcareinformatics, "What you See is What you Get", printed on May 22, 2002 http://www.healthcare-informatics.com/issues/1999/02_99/news.htm.
Kim Batch, "Who Needs a standard medical terminology . . . " Kim Batch Architect Center for Biomedical Informatics.
Hogarth, Michael A., Michael Gertz, and Fredric A. Gorin. "Terminology Query Language: a server interface for concept-oriented terminology systems." Proceedings of the AMIA Symposium. American Medical Informatics Association, 2000.
Apelon Products, printed on May 22, 2002 http://www.apelon.com/products/products . . . authoring.htm.
Brian J Love, "Un Edifact—an EDI standard for Health Care", Process in Standardization in Health Care Informatics, G.J.E. De Moor et al, IOS Press, 1993, pp. 156-161.
Georges J.E. De Moor, et al., "Towards a meta-syntax for medical edi", International Journal of Bio-Medical Computing, vol. 34, No. 1/4, pp. 319-330 (1994).
O.M. Kinkhorst, et al., "From medical record to patient record through electronic data interchange (EDI)", International Journal of Bio-Medical Computing. Elsevier Science Publishers, vol. 41, No. 1 Jul. 1996, pp. 151-155.
Jian-Yun Nie, "Unknown Word Detection and Segmentation of Chinese using Statistical and heuristic Knowledge", 1995, Communications of the Chinese and Oriental Languages Information Processing Society.
Y. Liu and Y. Satomura, "Building a Controlled Health Vocabulary in Japanese", Methods of Information in Medicine, 40:4 100', pp. 307-315. XP008026570 Abstract.
SMS "common Vocabulary Engine", Jul. 1999.
Siemens Medical, "Soarian knows System Architecture" Jan. 2002.
Siemens, "Siemens Reference Architecture Overview", Aug. 2003.
International Search Report of Application Serial No. PCT/US03/06766 dated Jan. 30, 2004.
Non-Final Office Action received for U.S. Appl. No. 10/379,880, dated Oct. 5, 2006, 15 pages.

\* cited by examiner

MEDICAL INFORMATION TRANSLATION SYSTEM

BACKGROUND

The present embodiments relate to medical information systems. In particular, the presentation of information assists users in understanding medical terms.

Each person has different models of the world based on their education, expertise and/or life experience. For example, a doctor has a greater medical vocabulary than a layman patient. The doctor may have more nuanced expressions, such as an Eskimo may have many words for types of ice while someone from an equatorial region may use merely "ice." Different people have different amounts of granularity in their model of the medical world.

People and organizations need to communicate despite these different levels or models of understanding and need. For example, a patient that is to have a total knee replacement receives a communication from a physician, such as a discharge order or a message in a patient portal (e.g., on-line or Internet-based messaging). The patient may not understand the word "edema" used by the physician. This term is not in the patient's model of the world. The patient may use "swelling," while a therapist may use "inflammation." A given message may contain whole sentences or multiple words leading to misunderstanding.

BRIEF SUMMARY

By way of introduction, the preferred embodiments described below include methods, systems, and instructions for communicating medical information between different entities. Personalized models of peoples' understanding of a medical field are created. Role information is used to create the personalized model. More information than mere role may be used for at least one of the personalized models, such as information on past medical history. The personalized models link to various subsets of base medical ontologies for one or more medical subjects. The concepts and relationships in these ontologies formed by the linking may be matched, providing a translation from one personalized model to another. The terminology with similar or the same concepts and/or relationships is output for a given user based on their model.

In a first aspect, a system is provided for communicating medical information between different entities. A healthcare database connects with a healthcare network of a medical facility. The healthcare database is configured to store roles for different users and different base models of ontologies for respective roles. A first computer connects with the healthcare network and is configured to receive input first information from a first user having a first one of the roles. A second computer connects with the healthcare network and is configured to output second information to a second user having a second one of the roles. The second role is different than the first role. The first computer, the second computer, or another computer translates the first information to the second information using first and second based models of the ontologies for the first and second roles. An input expression of the first information input from the first user is different than an output expression of the second information output to the second user, but the expressions communicate a same concept.

In a second aspect, a method is provided for communicating medical information between different entities. A processor creates a reader profile of a reader. The processor determines, based on the reader profile, an ontology personalized to the reader. The ontology personalized to the reader has terminology appropriate for the reader. The processor does the same for a writer. The processor identifies concepts from the ontology personalized to the writer for an expression input by the writer and locates concepts from the ontology personalized to the reader using the concepts from the ontology personalized to the writer. The processor outputs a re-expression of the expression input by the writer in the terminology appropriate for the reader. The re-expression is based on the concepts from the ontology personalized to the reader.

In a third aspect, a non-transitory computer readable storage media has stored therein data representing instructions executable by a programmed processor for use of a medical ontology for communicating medical information between different entities. The storage media includes instructions for obtaining profile information about a patient from a medical record database, creating a personalized ontology for the patient with links to different base ontologies, the links being based on the profile information, and outputting, to a printer or display, words from the personalized ontology.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
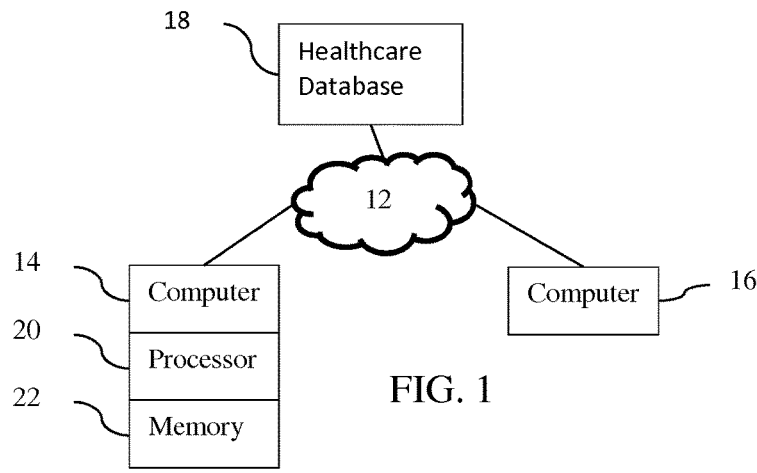
FIG. 1 is a block diagram of one embodiment of a system for communicating medical information between different entities.

Effective communication among care providers and patients is a prime contributing factor in quality of patient care. Communications are more effective and efficient when using terminology that more closely matches a person's model of the medical subject, level of understanding, and need.

Ontologies may provide packaging of knowledge and formal definitions of the knowledge for specific contexts (e.g., orthopedic surgery model). The ontologies provide the definitions at different levels of granularity. Medical ontologies provide information associated with one or more diseases and numerous medically relevant concepts (e.g., laboratory and diagnostic procedures; physiologic, biologic, genetic, molecular functions; organs and body parts; diseases, symptoms, and medical findings). Different relationships between concepts are reflected by the medical ontology. Concepts are organized within hierarchies that provide "IS A" type relationships (e.g., specific types of a disease are organized under more general types of a disease). Related morphologies (e.g., inflammation) and body location are other types of relationships in the medical ontology. Medical ontologies may also contain various terms associated with a medical concept representing the same (or similar) meaning for the concept.

Ontologies are generalized to subject, such as an ontology for orthopedic surgery. The ontologies do not account for different people's understanding or model of the subject. For example, the ontologies may not distinguish between terms used for a patient verses a therapist verses a primary care physician verses a surgeon or specialist.

By mining or otherwise searching for information about one or more of the people involved in communications, one or more personalized models may be created. Base ontologies are provided, such as ontologies for different roles and/or subjects. Using the information about the person, the personalized model is created by linking to the appropriate sub-sets of the base ontologies.

The concepts and/or relationships linked into the personalized models may be used to alter an input expression from one person to an output expression to another person. For a simple example, a physician inputs "edema." The personalized model for the physician links to a clinical base ontology for total knee replacement. In that base ontology, "edema" is linked to various relationships and concepts. These relationships, concepts and/or pattern of such are used to find the similar concepts, relationships and/or pattern in the patient's personalized model linked to a layman's total knee replacement ontology. The term "swelling" or terms "excess fluid" and "swelling" are output to the patient using the patient's personalized ontology.

The example above uses roles—patient and physician. In other examples, other roles with corresponding personalized models are used for translating expressions used in communication. Generalizing this problem to mere roles may also cause problems, such as where a patient has previously had a total knee replacement so should receive communications with a greater vocabulary rather than having the communications "dumbed down." More specific information may be used. For example, a patient is having a repeated total knee replacement. By finding this past medical history in the patient's medical record, the personalized model for the patient links to different base ontology information for some subjects. In the example above, the patient may be expected to know more refined terms, such as "inflammation" or "edema." As a result, the personalized model for the patient links to concepts in a base ontology for a therapist or physician for the subject of total knee replacement. When communications occur, "edema" is translated to "fluid inflammation" or "edema" based on the expectation that previous experience of the patient provides the understanding of the physician or therapist terms.

FIG. 1 shows a system for communicating medical information between different entities. The different entities may be people (e.g., patient, patient relative or caretaker, therapist, administrator, primary care physician, surgeon, nurse, or volunteer) or healthcare groups (e.g., physicians groups, hospitals, healthcare facilities). The different people and/or groups use different terminology or models of a given medical subject.

The system is used for communicating between these entities. For example, different entities may access a same record (e.g., patient record) in the healthcare database 18. One entity accesses a portal or application for reviewing information input by another entity. As another example, one entity may create orders or discharge papers that are to be read by another entity. In yet another example, one entity sends a message to another entity. Any communications using the network 12, one or more computers 14, 16, a display, and/or a printer may be provided. One entity enters an expression, such as a collection of terms, and the other entity is to read or receive (e.g., computerized read-out of the written words) the expressed information in an expression appropriate for the receiver's model of the subject.

The system includes a healthcare network 12, a computer 14, a computer 16, and a healthcare database 18. The healthcare network 12 interconnects the various components, but one or more direct connections (e.g., computer 16 being at or part of the healthcare database 18) may be used. The computer 14 is shown with a processor 20 and memory 22. Other computer components may be provided. The computer 16 has the same, similar or different components as the computer 14. Additional, different or fewer components may be provided. For example, a display or printer are provided with one or both computers 14, 16. As another example, only one computer 14 or 16 is used to enter an expression and to output another expression. In yet another example, additional computers are provided. The healthcare database 18 may not be provided.

The healthcare network 12 is an intranet, local area network, wide area network, Internet, enterprise network, or combinations thereof. Wired and/or wireless communications may be used. Routers route communications to or from various components of the network. The healthcare network 12 is for a medical facility, such as a hospital or network of hospitals, and/or other healthcare organization. Edge devices, such as routers or bridges, allow connection with other networks, such as connecting with an Internet service provider for access by a personal computer of a patient. Any now known or later developed healthcare network 12 may be used.

The healthcare database 18 is a memory, such as an array of RAM or other memory devices. The healthcare database 18 is one device or a collection of devices in one location. Alternatively, the database 18 is distributed to various locations. The healthcare database 18 may be part of a server or a server accessed database 18 for receiving additions to a medical record and/or for outputting stored medical record information. The healthcare database 18 may be owned and operated by a healthcare facility or is provided as a service to the healthcare facility.

In one embodiment, the healthcare database 18 is a computerized medical record for one or more patients. The computerized patient record includes clinical and/or diagnostic information related to care of a patient. The patient record includes values of variables available for a current patient. The variables correspond to features, such as medical history, pain indication, lump indication, age, genetic information, test results, family history, billing codes, medications, lab results, notes, text, or other sources of information. The patient record may include one or more images of a same or different type. Test results, orders, discharge, stored readings, and/or other information for a patient may be stored. The information may be from a given healthcare facility or may be gathered from various healthcare facilities. The patient record is input manually by one or more users and/or determined automatically. The patient record may be formatted or unformatted. The patient record resides in or is extracted from different sources or a single source. Any now known or later developed patient record format, features and/or storage may be used.

The healthcare database 18 may include other information, such as billing information. In one embodiment, the healthcare database 18 stores information about other users of the healthcare network 12. The healthcare database 18 may include other data stores than patient medical records, such as including employee information about physicians, nurses, administrators, and/or therapists. For example, log-in or access information and identity information (e.g., user name and password) are stored. As another example, a schedule, patient information, and other data usable by a healthcare provider (e.g., physician or nurse) are stored for access by the healthcare provider.

The healthcare database 18, either as one database or distributed as more than one database, is configured to store roles for different users. An application or other database management function causes collection and storage of roles. The log-in information or user identity includes an indication of a role of the person. Any roles may be used, such as patient or healthcare provider. In one embodiment, more than binary separation of roles is provided, such as patient, care provider for the patient, primary care physician, nurse, physical therapist, administrator, surgeon, and anesthesiologist. Additional, different, or fewer roles may be provided.

The healthcare database 18, either as one database or distributed as more than one database, is configured to store different base models of ontologies for the different roles. Alternatively or additionally, the base models are for different subjects (e.g., total knee replacement, medication, surgery, and general medicine).

Each base model is an ontology. Terms with corresponding concepts and relationships are logically connected. Any ontology and corresponding format may be used. Medical ontologies are provided in a structured format, with different links between different terms. Direct or "IS A" type relationships are linked. Site or body location relationships are linked. Morphology relationships are linked. Other relationships may include a cause, an effect, a symptom, a sign, drugs, tests, or a related disease. For example, diabetes may be shown as related to or connected with heart failure, but is not the same or an "IS A" relation. Diabetes may be related since a person with diabetes is more likely to have heart failure than a person without diabetes.

In one embodiment, the base models include a laymen ontology, a physician ontology and a therapist ontology. Other based models for other roles may be provided. A given base model may be for more than one role. The terms defined in the ontology are specific to the role. General terms not specific to the role may be included. The base models for the different roles reflect a generalized model of understanding, communications, terminology, vocabulary, and/or need for a given role. The base models are different, such as the layman's base model including "swelling" verses the physician's including "edema." Different levels of granularity may be provided in the different base models.

The different base models are for a same subject. For example, the base models are for total knee replacement. Other base models are provided for other subjects, such as heart surgery or stenting. Base models more generalized by subject may be provided, such as medication, surgery, and/or common clinical subjects.

Figure 2:
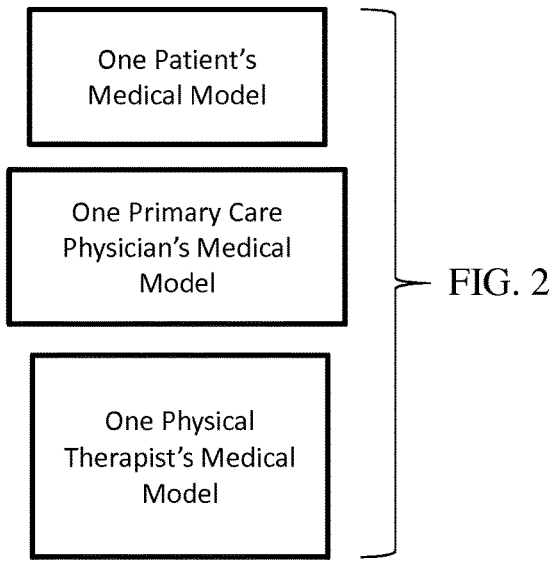
FIG. 2 shows an example of three personalized models.

The base models are used to create personalized models by role. For example, FIG. 2 shows a given patient's personalized medical model, a given primary care physician's medical model, and a given physical therapist's medical model. Different patients, physicians, and/or therapists medical models are the same or different.

Figure 3:
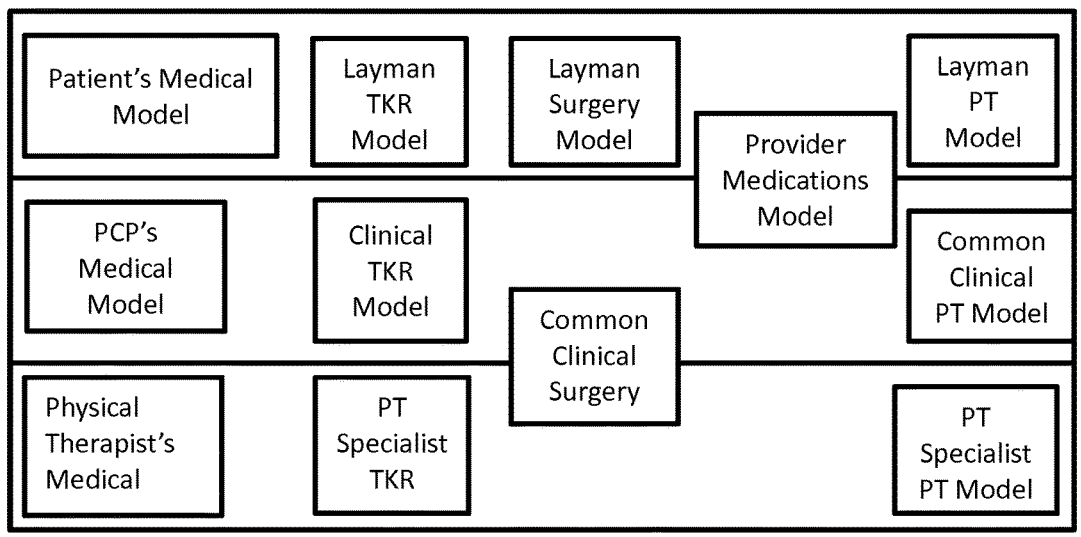
FIG. 3 shows an example of links to different base models for the three personalized models of FIG. 2.

The base models for one or more subjects are used to create a given personalized model. For example, FIG. 3 shows three personalized models of FIG. 2 in three horizontal rows. The base models used to form the personalized model for each are shown in the row. For the patient's personalized model, a layman's total knee replacement model (ontology), a layman's surgery model, a medication model, and a layman's physical therapy model are linked. For a primary care physician's personalized model, a clinical total knee replacement model, common clinical surgery model, medication model, and common clinical physical therapy model are linked. For a physical therapist, a physical therapist total knee replacement model, common clinical surgery model, and physical therapist physical therapy model are linked. Additional, different, or fewer ontologies may be linked. The database 18 stores the links.

The computers 14, 16 are workstations, nurse's stations, physician computers, tablets, servers, personal computers, or other processing device for accessing, inputting, and/or outputting information, such as patient specific information from the healthcare database 18. The computers 14, 16 connect with the healthcare network 12, such as a direct link as part of the hardwired network or an indirect link through other networks. The computers 14, 16 are located in the medical facility, such as being workstations in the medical facility. In other embodiments, one or both of the computers 14, 16 remotely access the healthcare network 12, such as a personal computer, smartphone, or tablet being used by a patient or care provider of the patient at a house.

The processor 20 is a general processor, digital signal processor, application specific integrated circuit, field programmable gate array, analog circuit, digital circuit, combinations thereof or other now known or later developed processor. The processor 20 may be a single device or a combination of devices, such as associated with a network or distributed processing. Any of various processing strategies may be used, such as multi-processing, multi-tasking, parallel processing or the like. The processor 20 is responsive to instructions stored as part of software, hardware, integrated circuits, film-ware, micro-code or the like.

The processor 20 operates to receive input information from a user. A writer, such as a physician, nurse, patient or other person, inputs an expression into the computer 14. The expression may be free text or selection of structured text (e.g., selecting an input from a drop down list). Using a user input device, such as a keyboard and/or mouse, the processor receives input information. The input information is entered by a user known to the processor 20 or database 18, such as based on log-in. The input information is specific to a patient, such as for a total knee replacement patient. The input information is for a communication, such as for a message from a physician to a patient or a data entry into the medical record for the patient to be viewed at a later time.

The memory 22 is a non-transitory computer readable storage media. Computer readable storage media include various types of volatile and non-volatile storage media, including but not limited to random access memory, read-only memory, programmable read-only memory, electrically programmable read-only memory, electrically erasable read-only memory, flash memory, magnetic tape or disk, optical media and the like. The memory 22 may be a single device or a combination of devices. The memory 22 may be adjacent to, part of, networked with and/or remote from the processor 20. The memory 22 is separate from the database 18, but may be part of the database 18.

The memory 22 may store the base models, personalized models, expressions, terms, and/or information from the database 18. The memory 22 may store a mining engine. The mining engine includes a domain-knowledge base or rules used for searching the database 18 to create the personalized model or models. The mining engine is software, code or other instructions for mining one or more patient records. The mining engine is operable to mine the medical record as a function of the domain-knowledge base. The mining engine searches in structured and/or unstructured data of the medical record.

The memory 22 may be a computer readable storage media having stored therein data representing instructions executable by the programmed processor 20 for communicating between two entities. The memory 22 stores instructions for the processor 20. The processor 20 is programmed with and executes the instructions. The functions, acts, methods or tasks illustrated in the figures or described herein are performed by the programmed processor 20 executing the instructions stored in the memory 22. The functions, acts, methods or tasks are independent of the particular type of instructions set, storage media, processor or processing strategy and may be performed by software, hardware, integrated circuits, film-ware, micro-code and the like, operating alone or in combination.

The other computer 16 is configured to output information on a display. Alternatively, a printer for the computer 14 or other output is provided for outputting information. The information is output for a user different than the one inputting the information. The recipient may have input some of the output information, but at least some is from a different user. The computer 16 is configured to output information from a user having one role to a user having a different role. Alternatively, the users have the same role, but different personalized models.

The computer 14, 16 may include a display, such as a CRT, monitor, flat panel, LCD, projector, printer or other now known or later developed display device for outputting written information. For example, the processor 20 causes the display 16 at a local or remote location to output data indicating a possible diagnosis, readings, test results, case summary, discharge order, therapy order, lab order, other order, other results, or other medical information (e.g., an annotated image or other information from a medical record of a patient). The output may be stored with or separate from the patient record.

Various information is input for review or output. The output is later or immediate. For example, a user inputs information to a medical record for a patient. The patient or a different user later accesses the information. The patient or other user access may be only of the information input at that one time or may be of a collection of information input by one or more other users over time.

The information as input may be expressed using terms for the source or writer. For the target or later accessing user, a different expression or terms may be more likely to be understood. The information is translated from the input expression to a different output expression. Any processor may be used for this translation. For example, the translation is by the input computer 14. The translation occurs immediately after or during input of the information or the translation occurs later. As another example, the translation by the output computer 16. The translation occurs upon access. In another example, a separate server or other computer (e.g., server associated with the database 18) performs the translation at any time, such as when the information is accessed. In the further discussion below, the processor 20 is described as creating the personalized models and/or translating using personalized models. Other processors may be used.

Similarly, any of the input computer 14, the output computer 16, or another processor creates one or more personalized models. For translation, one or more personalized models for the source (writer) of the information and one personalized model for the target (reader) are used. These personalized models may be created as needed for or during translation (i.e., performed as part of the translation). Alternatively, the personalized models are created at other times, such as when a new user or login is created, when a writer inputs, when a reader accesses, and/or as part of a batch process.

The processor 20 is configured to implement a communications model. The communications model is an application, program, or other approach for communicating. For example, the communications model is a messaging program, patient portal, patient medical record program, workstation with a printer driver, or other mechanism using the system of FIG. 1 to communication information input from one or more sources to a target.

The communications model identifies the appropriate subject matter. The processor identifies the subject matter based on user selection, patient information, and/or the identity of the source. For example, a patient having or recently having had a knee replacement is used to identify the subject as total knee replacement. As another example, a physician with a specialty, such as knee replacements or orthopedics identifies the subject as knee replacement or orthopedics. Other sources of the subject may be provided, such as rules searching for specific billing codes or diagnosis information. The nature of the use of the system of FIG. 1 may indicate the subject, such as a patient logging into a patient portal for heart attack patients. Any resolution of subject may be used, such as orthopedics, knee surgery, or total knee replacement.

The subject matter defines a set of one or more base models of ontologies to use. For example, base ontologies for total knee replacement or other subject are selected based on the same subject. Other base ontologies may be associated with a given subject, such as also or instead of including common or generalized surgery, medication, and orthopedics ontologies.

There are at least two users in a given communication, so at least two personalized models are created. An ontology reflecting a given user's likely model of understanding the subject is created. The processor 20 is configured to construct personalized models for the users. To link specific parts of the base models to a given user for personalization, data about the user is gathered. To create the personalized model or ontology, the processor 20 is configured to mine or otherwise search the database 18 for data about the user. A set of rules may be used to guide the search or mining. For example, a rule set defines the possible subjects and relevant data for each given subject. Some example relevant data is whether the patient has had a previous operation of the same type, an education level of the person (e.g., greater vocabulary for more educated or specific vocabulary for specific specialty education), and the sex of the person (e.g., greater or lesser knowledge about specific anatomy). The relevant data is the same or different for users with different roles.

The database 18 is mined for the relevant data. The processor 20 is configured to apply a mining engine to a medical record or other information in the database. The mining engine uses a domain knowledge base, such as rules with information about field or structure of the database or evidence to support a conclusion about the user. For example, the mining engine searches for specific terms in structured and/or unstructured portions of the medical record. The mining may locate terms and/or may infer information, such as a patient state or diagnosis.

Based on the mining or other searching, the processor 20 identifies subsets of base models of the ontologies for the subject. The rules indicate the subsets. For example, a rule indicates a search criterion as the sex of the patient. If male, then a subset of definitions related to female and male anatomy in one or more base ontologies is linked (e.g., more granular or greater vocabulary for male-related terms and lesser for female-related terms). If female, a different subset of definitions related to female and male anatomy in one or more base ontologies is linked (e.g., more granular or greater vocabulary for female-related terms and lesser for male-related terms). As another example, a rule indicates a search criterion as previous medical history of a total knee replacement. If yes, then a greater knowledge and corresponding vocabulary is linked (e.g., linking terms from a physician's or therapist's total knee replacement ontology). If no, then a lesser knowledge and corresponding vocabulary is linked (e.g., linking a layman's total knee replacement ontology). In yet another example, previous use of medication in general or a specific medication is identified for a patient. This medication information may indicate a base medication ontology to use, such as for communicating whether the patient is to administer their own mediation or not.

Using any number of variables, different subsets of definitions likely known to the user are linked into a personalized ontology. Different parts of the base ontologies are assigned to the user. The personalized model or ontology is formed by links to one or more base ontologies. Each link is to a definition or sub-set of definitions of the base ontology. All of a base ontology may be linked to a given user. Alternatively, the selected sub-sets are copied to create the personalized ontology.

Each person has different models of the world based on life experience. The personalized medical model is created to approximate a person's level of knowledge for a relevant context/subject matter (e.g., total knee replacement). By classifying and linking information about a person (patient or provider) to relevant general role-based knowledge models, the processor automatically builds a more personalized model. The mined information for a user is used to create the personalized model or ontology. The user is profiled as having different levels of knowledge for different areas of a given field or subject. For example, a patient may have layman's knowledge for surgery, but greater knowledge regarding knee anatomy based on a previous diagnosis of a knee condition and therapy without having had surgery. The processor 20 uses this profile to link surgical terms to a layman's surgical ontology but knee anatomical terms to a therapist's total knee replacement ontology.

The linked definitions from various base ontologies indicate likely or profiled knowledge and corresponding definitions of terms in a common terminology (ontology). The base ontologies provide concepts and relationships appropriate for each linked definition or term. Where a subset linked from one base ontology includes a same term or definition as a subset linked from another base ontology, a ranking system may be used. For example, rules weight or define which ontology to use for that term. To increase understanding, the least granular or simpler ontology may be used. Alternatively, an education level or identified role may dictate using a specialized ontology instead of a more generalized ontology definition. This may result in more granular definitions appropriate for expertise of the user, allowing for more exact communication.

FIG. 2 shows an example of creating three different user models—a given patient, a given physician, and a given therapist. Personalized models may be created for additional, different, or fewer users. The personalized model for a given user may be the same or different than a personalized model for another user with the same role. For example, two total knee replacement patients with no previous history of knee replacement or surgery and no other indicators of more advanced knowledge have a same personalized model. Another total knee replacement patient had a previous knee replacement, so have at least one different link and corresponding definition than the other two patients is provided. A different base ontology is used for at least one definition.

FIG. 3 shows example base ontologies linked to the personalized ontologies. In this example, the patient's medical model is linked to definitions in a layman's total knee replacement model, a layman's surgery model, a layman's physical therapy model, and a provider's medications model. The physician's model is linked to definitions in other models expect for the same medication model, and the physical therapist's model is linked to definitions in yet other base models except for the same clinical surgery model. A physician, patient, and therapist have different links to the same or different base ontologies than the others.

The processor 20 is configured to translate information from one or more sources to information output to a target. The translation is performed for each of any targets accessing the communication. Information from one or more users (e.g., writers) is translated for output to another user (e.g., reader). For example, a physician accesses a patient medical record. Information previously input by others may be included in the accessed information. The processor 20 translates the expressions input by others into an expression more likely appropriate for the physician. The expressions or groups of terms used for the same ideas or concepts may be different for different users. The expressions communicate the same concept or concepts. For example, a physician enters "edema" into the medical record or a discharge order. The processor 20 translates "edema" to "swelling caused by blood build-up" for a patient to read the discharge order.

The personalized models are used in the translation. The linked concepts and relationships from the base models included in the personalized models are used in the translation. The processor 20 accesses the personalized model of a source of information, such as a physician's personalized model for the physician that entered diagnosis notes. The personalized model provides links to definitions from base ontologies for the terms or words in the expression used by the physician in entering the information (e.g., physician enters "edema" in a medical record, and the personalized model for the physician links to a common surgical model (base model) for the definition of "edema").

The processor 20 determines an output based on the personalized model and corresponding links to base models for the reader, such as the patient. The output expression uses replacement terms for the medical terms of the input expression.

For translation, the personalized models are derived from common sets of base models, such as base models dealing with the same subject or subjects. The information is translated from one personalized model to another personalized model. A relevant sub-set of definitions of one personalized model is translated to a sub-set of definitions of the other personalized model. In one embodiment, an expression to be translated is decomposed. Semantic or other parsing is applied. The expression is broken down into terms provided as definitions in the ontology. The expression is divided into different concepts. The personalized model of the source may be used to identify the concepts for the terms or expression used. Relationships, concepts, and/or other ontology information are found for the input expression.

This pattern, the concepts, and/or relationships from the personalized ontology for the input expression are recursively introspected. The base ontologies may provide tree or level structures with concepts for a definition being further broken down. The processor 20 recursively looks for matching concepts, relationships or patterns in the personalized model of the reader. The operation is recursive since the operation may be repeated at different levels. Some concepts may be found at one level and other concepts at a different level. Alternatively, all of the concepts are found at the same level. The processor 20 introspects by matching the concepts. The matching is performed for the desired level of granularity. The formal concept definition expressions from the input are built from other concepts and relationships for the output. Once all or a sufficient percentage of the concepts, relationships, patterns, or combinations thereof are found, the processor 20 has a match usable for translation. Other translation approaches may be used.

The concepts, relationships, or patterns thereof in the definition may be aligned across the personalized models. Where an exact match is not located, a match that subsumes the concept from the source is identified. Semantic query or other operations are used to discover more specific or subsuming concepts or further decomposed.

The translations are performed by looking up definitions of terms in the input expression, such as looking up buzzwords. This look-up is used to match the input expression with defined terms in the readers' personalized model (e.g., terms in a vocabulary that a reader will understand). The output is a re-expression of what the writer has written. Using the personalized ontologies, the output expression is in language that the reader may understand.

The input expression may have a different or same granularity for a concept than the output expression. The differences in granularity may reflect differences in the linked base models. Some difference in granularity may be acceptable, such as outputting "swelling" instead of communicating that the swelling is caused by fluid (e.g., an "edema"). Alternatively, the same level of granularity as the input is output, but with a different expression (e.g., edema is input and "liquid caused swelling" is output).

A feedback mechanism may be provided. The reader may indicate a lack of understanding for one or more terms in the output expression. The processor 20 uses the feedback to re-create the personalized model. For example, the personalized model is altered to link to more layman base models instead of other models. The processor 20 then re-performs the translation to assist the reader. The feedback may be automated, such as monitoring whether the patient acts appropriately based on the output expression. For example, the output expression on an order given to a patient is to "ingest warfarin". If the pharmacy records later indicate not filling a prescription for warfarin, this feedback is used to re-express (e.g., "take a prescription for the drug warfarin") the output instructions to the patient.

The base ontologies may be in one language, such as English. For patients or other users most comfortable or desiring the input and/or output in a different language, the processor 20 may convert the expression into the desired language. For example, the output expression created by translation is changed from English to German. Any language translator may be used.

Figure 4:
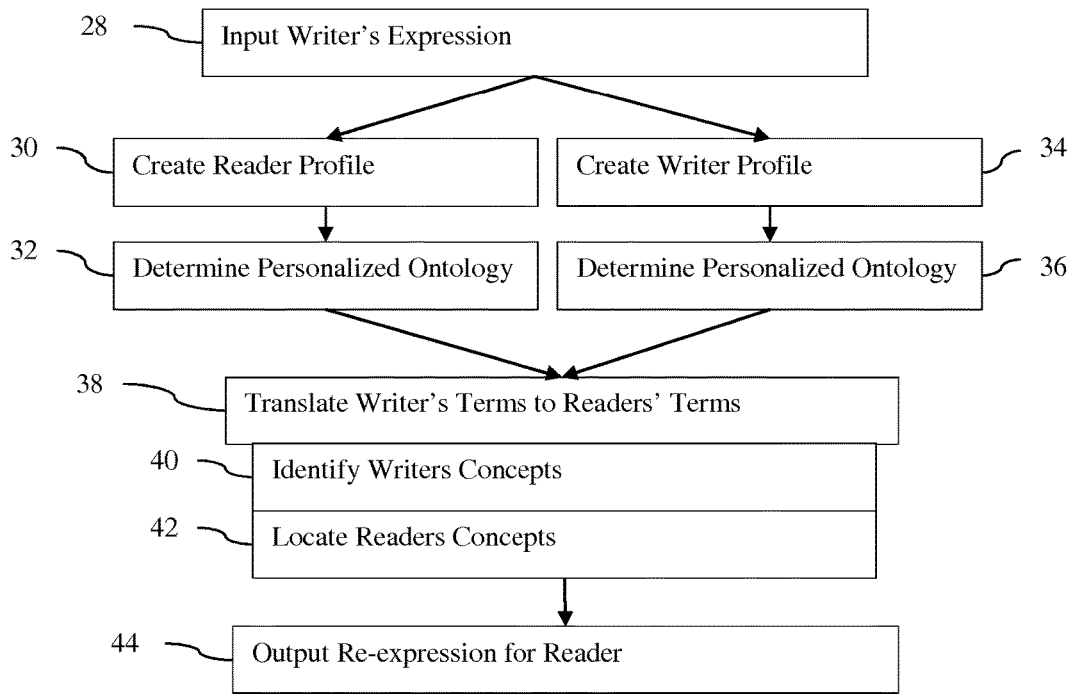
FIG. 4 is a flow chart diagram showing one embodiment of a method for communicating medical information between different entities.

FIG. 4 shows one embodiment of a method communicating medical information between different entities. The method is implemented by the processor 20 of the computer 14, a different processor, a different computer, or other server. Different acts may be implemented by different devices, such as a database storing information while a processor creates personalized models and translates. Input devices, output devices, and a network are used to communicate.

Additional, different or fewer acts than shown in FIG. 2 may be provided. For example, acts 30-36 are not performed and a generalized ontology or ontologies are used. In another example, personalized ontologies are created in acts 30-36 without performing a translation in act 38. In yet another example, acts for identifying subject matter are performed.

The acts are performed in the order shown or a different order. For example, acts 34 and 36 are performed before, after, or simultaneously with acts 30 and 32.

In act 28, a written expression is input. A user, such as a physician, patient, therapist, or other healthcare provider inputs an expression using an input device. The expression is input to a computer and recorded in a database or locally to the computer. In alternative embodiments, the input expression is audio, which is converted to written.

The input is in any format, such as inputting unstructured text as notes, a sentence, or clause. In one embodiment, the input may be structured, such as selecting available options for a field. The options available for selection may be based on an identity of the writer. The expression is of any length, such as being a page, paragraph, sentence, clause, or single word.

More than one expression may be input. For example, a physician or nurse inputs various fields of information. These different expressions are input in a same session or may be input in different sessions over time by the same or different writers.

The input is into a medical record for a patient. One or more of the input expressions may be to other databases, such as billing, note taking, or physician databases. The input may be in an application or program for communicating with others, such as a patient portal system.

In act 30, a reader profile is created. The processor mines or otherwise searches a patient medical record database or other database of reader information. The role of the reader with or without other reader information (e.g., medical history, diagnosis, expertise, or years of experience) is used to create the profile.

Rules are used to establish the profile. The rules indicate the information sought from the database about the reader and how that information is to be used. A profile with information used to determine a likely model for communications for a given subject is developed.

In act 32, the processor determines an ontology personalized to the reader. The reader profile is used to determine terms or definitions likely in the readers' understanding. The rules for the profile define definitions to use for that reader. For example, a medical history from a patient medical record database indicates more advanced terms due to previous medical experience. As another example, a lack of previous experience indicates layman terms or definitions to be used in the personalized model.

The ontology personalized to the reader has terminology appropriate for the reader. The profile indicates the terminology appropriate to the reader. The indication is implemented as links to sub-sets of other medical ontologies. For example, different ontologies are provided for different roles in a same subject matter. Based on the role information in the profile, the definitions or terms in the appropriate role ontology are used to form the personalized ontology. Based on other information than role, some of the links may be redirected to other ontologies. Different terms may be linked to different ontologies. Which ontologies to use are indicated by the profile and corresponding rules.

The stage in the process of care may indicate which ontologies to use for some or all of the terms. For example, the profile indicates that a patient is in a surgery planning stage of the care process. For surgery related terms, an ontology related to surgery is linked to the patient's personalized model.

In act 34, a writer profile of a writer of input expressions is created. The processor creates a profile for the source entity. The same or different creation process as used for the reader is applied. The profile is created from available database information. Where multiple authors contributed to the expression or expressions to be translated, multiple writer profiles are created.

In act 36, the processor determines an ontology personalized to the writer. The writer profile indicates the ontologies to use. An ontology personalized to the writer has terminology appropriate for the writer. For example, the processor links to sub-sets of medical ontologies for different roles in a same subject. The determination of the personalized ontology for the writer is the same or different process as used for the reader. A personalized ontology is created for each contributing writer.

In act 38, the writer's or writers' terms from the input expression or expressions are translated to reader's terms. For example, the processor translates an expression from a healthcare worker into the words of a patient using the personalized ontologies for the healthcare worker and the patient.

Acts 40 and 42 represent one approach for translating. Additional, different, or fewer acts may be used.

In act 40, the processor identifies concepts and/or relationships from the ontology personalized to the writer for an expression input by the writer. For example, a physician enters an expression. The medical terms in the expression are found and concepts or relationships from the ontology for the medical terms are identified.

The expression is decomposed into terms or words. Semantic processing may be used. Prepositions, conjunctions, or other non-medical words may be removed. The remaining medical terms may be in the personalized ontology. Where the expression is made of terms from a fixed vocabulary, such as associated with entries into structured fields of the database, the base ontologies may be assured to define the words of the expression. Alternatively, each word of the expression is searched for in the personalized ontology. Found terms are treated as medical terms for translation and other terms are not.

The communications model may identify one or more goals. For example, the goal is discharge or filling a discharge order template. Accordingly, the communications model searches for words expected in discharge. The goal, subject, or other information may be used to limit the number of words being searched for or being searched.

The expression is classified by finding the concepts and/or relationships for the decomposed words found in the personalized ontology of the writer. The concepts, relationships, and/or a pattern of concepts and relationships are extracted from the personalized ontology. Any number of levels may be extracted, such as just the first level (e.g., one link or relationship to the word being defined). The number of levels for different concept branches in the personalized ontology may vary based on the matching. Concepts related to first level concepts may be searched for any first level concept not matched with the reader's personalized ontology.

In act 42, the processor locates concepts, relationships, or patterns of concepts and relationships from the ontology personalized to the reader using the concepts, relationships, or patterns of concepts and relationships from the ontology personalized to the writer. Words or terms with similar definitions as in the writer's ontology are found in the reader's ontology. Due to differences in granularity, the number of words may increase or decrease.

Any matching or similarity measure may be used. For example, a match is found for each concept. The matching may include semantic measures, such as matching a noun concept to a noun concept. The matching may include fuzzy logic, Bayesian network, or other classifier for measuring similarity of the meaning of words.

In one embodiment of the matching, recursive introspecting is used. The first level concepts are searched for the same or similar concept in the reader's ontology. If a match is not found, then the concepts related to the unfound concept in the writer's ontology are searched for in the reader's ontology. The process iteratively continues until a sufficient number of matches are found. This aligns the concepts from the ontology personalized to the writer with the concepts from the ontology personalized to the reader. Source or writer concept expressions are translated into target or reader expressions by mining out formal definition expressions.

Each concept, relationship, or pattern (e.g., concept and relationship) is matched separately. Alternatively, concepts with certain types of relationships (e.g., "is a") are matched together, such as searching until one member of the group is found for "or" conditions. Concepts with other relationships may be searched as a linked group or pattern to maintain meaning.

Due to differences in granularity, the matching may allow for more general or the same granularity. A ranking of granularity may be provided, such as a percentage of the concepts for a definition that are located. More specific concepts or expressions may be searched for in the reader's ontology to better match the granularity of a term from the writer's ontology. Once a sufficient number of concepts are located in the reader's ontology, the granularity for the translation is satisfied. The communications model may set the level of granularity, such as in response to user configuration.

Once matched, the concepts identified from the reader's ontology are used as the translation. Defined terms for the matched concepts are selected and used as the translation. For example, the reader's ontology terms "swelling caused by liquid" replaces the writer's ontology term "edema." The terms are inserted into the same sentence or structure as the written expression. For example, the writer's expression "call if you notice an edema" is translated to "call if you notice swelling caused by blood."

Where multiple reader terms are provided for a given writer's term, the order is based on the order and/or relationships from the definitions in the writer's ontology and/or based on the order of the starting terms in the writer's expression. Semantic or other processing may be applied to order the terms as appropriate.

Where granularity differences resulted in generalization, the matched concepts from the reader's ontology may be searched for repetition. More generalized or equivalent concepts or expressions are avoided (e.g., "he had a 'fever' and he had an 'extremely high body temperature'").

When the reader uses a language different than the writer or the base ontologies, the translated expression is further translated into the appropriate language. A natural language translator is applied by the processor to the writer-to-reader translated expression.

In act 44, the re-expression of the expression input by the writer or writers is output. The re-expression is an expression in terminology appropriate for the reader. The reader profile is used to create the personalized ontology. Based on the personalized ontology, an expression using concepts or terms likely to be understandable to the reader is translated from the expression or expressions input by others. The re-expression is based on concepts from the ontology personalized to the reader. Words from the personalized ontology of the reader are output instead of words input by one or more other writers. For example, an expression input by a physician is output as an expression for a layman, patient, therapist, administrator, or nurse.

Some of the input words, including medical terms, may be left the same, but other words are replaced. Alternatively, all of the medical terms are replaced. The replacement depends on the personalized ontology of the writer as compared to the personalized ontology of the reader.

The output is to a display or printer. The output is the expression in the form of text. The text is output in fields in a template. Alternatively, the text is output in clauses, sentences, paragraphs, or other unstructured format corresponding to the original input. The display or printer is configured to output the expression for reading by the reader. In alternative embodiments, the output is to a processor and speaker. The processor outputs audio to the speaker. The audio is converted from the expression.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A system for network-based communication of medical information between different entities, the system comprising:
   a healthcare database configured to store roles for a first user and a second user, login credentials used by each of the first user and the second user to access the healthcare database, and different base models of ontologies for their respective roles;
   a first computer in communication with the healthcare database through an internet computer network, the first computer configured to receive an input first expression from a first user having a first one of the roles, the first expression communicating a healthcare concept; and
   a second computer in communication with the healthcare database through the internet computer network, the second computer configured to output a second expression to a second user having a second one of the roles, the second role different than the first role, the second expression communicating the healthcare concept, and wherein the first expression necessitates translation into the second expression to enable the second user to understand the second expression;
   wherein the first computer or the second computer perform actions comprising:
   selecting the second user as a target of the second expression from a healthcare group, the selecting based on an identity of the first user and a context of a communication sent by the first user to the healthcare group;
   subsequent to the selecting, determining roles of each of the first user and the second user based on the login credentials used by each of the first and the second users to access the healthcare database;
   assigning, based on the determined role of each of the first and second users and the context of the communication, at least a first base model ontology to the first user and at least a second base model ontology to the second user, the first base model ontology being different than the second base model ontology;
   creating, by mining the healthcare database for data about the first user and the second user, each of a first personalized ontology model by linking to first subsets of a first base model ontology and a second personalized ontology model by linking to second subsets of a second base model ontology, wherein the first personalized ontology model is automatically created by data available to the processor about the first user and the second personalized ontology model is automatically created by data available to the processor about the second user;
   upon receiving an indication that the second computer in internet communication with the healthcare database has requested the healthcare concept for the second user, translating the first expression to the second expression by using the first personalized ontology to decompose the first expression into the healthcare concept and the second personalized ontology to re-express the healthcare concept into the second expression, the first expression being different than the second expression; and
   transmitting the second expression to the second user.

2. The system of claim 1 wherein the healthcare database comprises a computerized patient record.

3. The system of claim 1 wherein the first computer comprises a workstation of the medical facility and the second computer comprises a personal computer.

4. The system of claim 1 wherein the first role is a physician, nurse, or physical therapist and wherein the second role is a patient.

5. The system of claim 1 wherein the different base models comprise a layman ontology, a physician ontology, and a therapist ontology, the input expression having a different granularity for the concept than the output expression, the different granularity reflected in differences in the different base models.

6. The system of claim 1 wherein the different base models of the ontologies are for a same subject matter identified by a communications model.

7. The system of claim 1 wherein the different base models of the ontologies are for the different roles for each of a plurality of different healthcare subjects.

8. The system of claim 1 wherein the first computer, the second computer, or another computer is configured to translate by recursive introspection of concepts and relationships in the ontologies.

9. The system of claim 1 wherein the first computer, the second computer, or another computer is configured to translate by semantic query.

10. The system of claim 1 wherein the first computer, the second computer, or another computer is configured to convert the output expression of the second information into a language of the second user.

11. The system of claim 1 wherein the first user is a healthcare worker using medical terms in the input expression of the first information, and wherein the second user is a patient reading the output expression of the second information, the output expression using replacement terms for the medical terms.

12. The system of claim 1, further comprising a third computer connected with the healthcare network, the third computer configured to output third information to a third user having a third role, the third role different than the first role and the second role, wherein the first computer or the third computer perform actions comprising:
   selecting the third user as a target of the third information;
   determining the roles of each of the first and the third users based on a login credential used by each of the first and the third users;
   assigning, based on the determined role of each of the first and third users and a context of the communication, at least a first base model ontology to the first user and at least a third base model ontology to the third user, the first base model ontology being different than each of the second and third base model ontologies;
   translating the first information to the third information using the first and the third base models of the ontologies for the first and third roles, an input expression of the first information input from the first user being different than an output expression of the second information output to the second user and different than an output expression of the third information output to the third user, but the three expressions communicating a same concept.

13. The system of claim 12, wherein the second user and the third user are members of a common healthcare group.

14. A computer-implemented method for communicating medical information between different entities, the method comprising:
   selecting a second user from a healthcare group, the selecting based on an identity of a first user and a context of a communication sent by the first user to the healthcare group;
   subsequent to the selecting, determining a first role of the first user and a second role of the second user, the determining based on login credentials used by each of the first user and the second user to access medical information on a healthcare network of a medical facility;
   assigning a first base model ontology to the first user and a second base model ontology to the second user, wherein the assigning is based on the determined roles of each of the first and the second users and the context of a communication between the first user and the second user;
   creating, by mining a healthcare database for data about the first user and the second user, a first personalized ontology model by linking to first subsets of a first base model ontology and a second personalized ontology model by linking to second subsets of a second base model ontology, the first personalized ontology model automatically determined by data available to the processor about the first user and the second personalized ontology model automatically determined by data available to the processor about the second user;
   translating, using the first personalized ontology model and the second personalized ontology model, a first information input by the first user having the first role to a second information to output to the second user having the second role, the first information being different than the second information but communicating a same concept; and
   transmitting the second information to the second user.

15. The method of claim 14, wherein the data mined and used to create each of the first personalized ontology model and the second personalized ontology model comprises: treatment experience of each of the first and the second user, education of each of the first and second user, specialization of the second user, and gender of the each of the first and second user.

16. The method of claim 15, wherein the data mined and used to create at least the first personalized ontology model comprises a patient profile on the healthcare network and an electronic medical record.

* * * * *